United States Patent [19]

Terao et al.

[11] Patent Number: 4,780,549
[45] Date of Patent: Oct. 25, 1988

[54] ASCORBIC ACID DERIVATIVES AND THEIR PRODUCTION

[75] Inventors: Shinji Terao; Minoru Hirata, both of Osaka, Japan

[73] Assignee: Takeda Chemical Industries, Ltd., Osaka, Japan

[21] Appl. No.: 149,895

[22] Filed: Jan. 28, 1988

Related U.S. Application Data

[63] Continuation of Ser. No. 683,136, Dec. 18, 1984, abandoned.

[30] Foreign Application Priority Data

Dec. 19, 1983 [JP] Japan ................................ 58-240741

[51] Int. Cl.$^4$ ............................................ C07D 307/62
[52] U.S. Cl. ............................................................ 549/315
[58] Field of Search .......................................... 549/315

[56] References Cited

U.S. PATENT DOCUMENTS 4,552,888 12/1985 Koppel et al. ...................... 549/315

FOREIGN PATENT DOCUMENTS

| 7095 | 7/1979 | European Pat. Off. |
| 86554 | 1/1983 | European Pat. Off. |
| 8200644 | 3/1982 | Int'l Pat. Institute ............. 549/315 |
| 0098954 | 7/1978 | Japan .................................. 549/315 |

OTHER PUBLICATIONS

Chemical Abstracts vol. 100, p. 608, 100:51926x, 1984.
Publication of Patent Application in Republic of South Africa, Publication No. 76/1944, Andrew John Tofe.
Proceedings of the National Academy of Sciences of the U.S., vol. 47, pp. 1875–1880 (1961), Martin G. Ettlinger et al.
Canadian Journal of Chemistry, vol. 47, pp. 2498–2501 (1969), K. G. A. Jackson et al.
Canadian Journal of Chemistry, vol. 43, pp. 450–457 (1965), K. G. A. Jackson et al.

*Primary Examiner*—John Kight
*Assistant Examiner*—Nathan M. Nutter
*Attorney, Agent, or Firm*—Wegner & Bretschneider

[57] ABSTRACT

An ascorbic acid derivative of the formula:

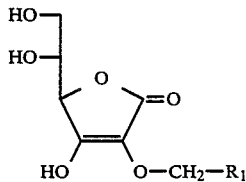

wherein $R_1$ is an organic residue having a molecular weight of from 58 to 400 is novel compound and is useful as antioxidant agent for food.

9 Claims, 1 Drawing Sheet

Fig. 1

ASCORBIC ACID DERIVATIVES AND THEIR PRODUCTION

This application is a continuation of U.S. Ser. No. 683,136, filed Dec. 18, 1984, now abandoned.

The present invention relates to an ascorbic acid derivative, its production and use.

Ascorbic acid possesses oxidation preventive activity, and is used in foods for the purposes of prevention of browning, retention of flavor, preservation of freshness, and the like.

However, ascorbic acid is susceptible to degradation, and encounters in some instances difficulties in producing the above-mentioned effect over a prolonged period of time.

Under these circumstances, the present inventors conducted extensive research with a specific view to obtaining an ascorbic acid derivative which is less susceptible to degradation and also possesses adequate oxidation preventive activity, and as a result, found that modification of the 2-position of ascorbic acid with a group having a relatively large molecular weight can yield a compound which achieves the desired object. The finding was followed by further research, which has culminated in the present invention.

The present invention is directed to:

(1) An ascorbic acid derivative of the formula:

wherein $R_1$ is an organic residue having a molecular weight of from 58 to 400, (2) A method for producing an ascorbic acid derivative [I], which comprises subjecting a 5,6-acetal or ketal derivative [II] of a compound [III] of the formula:

wherein $R_1$ is as defined hereinbefore and $R_2$ is a group removable by hydrolysis or reduction] to hydrolysis and/or reduction; and (3) Antioxidant preparations for food which contains an ascorbic acid derivative.

In the above formulae, the organic residue having a molecular weight of from 58 to 400 as represented by $R_1$ includes, for example, straight-chain or branched alkyl groups, straight-chain or branched alkyl groups which have a substituent or substituents, alkenyl groups which may have a substituent or substituents, aryl groups which may have a substituent or substituents, aralkyl group which may have a substituent or substituents, acyl groups which may have a substituent or substituents, aryloxy groups which may have a substituent or substituents and aralkyloxy groups which may have a substituent or substituents.

The above straight-chain or branched alkyl group having a molecular weight of from 58 to 400 is preferably those having 5 to 22 carbon atoms, more preferably those having 9 to 20 carbon atoms.

Examples of such alkyl groups include, for example, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nondecyl, n-eicosyl, n-heneicosyl and n-docosyl.

The alkyl in the above straight-chain or branched-chain alkyl groups having a molecular weight of from 58 to 400 which have a substituent or substituents is preferably those having 1 to 10 carbon atoms.

Examples of the said alkyl group include, for example, methyl, ethyl, n-propyl, isopropyl, n-butyl, isobutyl, sec-butyl, tert-butyl, n-pentyl, n-hexyl, n-heptyl, n-octyl, n-nonyl and n-decyl.

The above substituent includes, for example, lower alkoxycarbonyl groups, aryl groups which may have a substituent or substituents, aralkyl groups which may have a substituent or substituents, arylcarbonyloxy groups which may have a substituent or substituents, aralkylcarbonyloxy groups which may have a substituent or substituents, 2,3,5-trimethyl-1,4-benzoquinoyl group, 2,3-dimethoxy-5-methyl-1,4-benzoquinoyl group and 2-methyl-1,4-naphthoquinoyl group.

The alkoxy in the said lower alkoxycarbonyl groups is preferably those having 1 to 6 carbon atoms, and examples of such alkoxy groups includes, for example, methoxy, ethoxy, n-propoxy, n-butoxy, n-pentoxy and n-hexoxy.

The aryl group in said aryl groups which may have a substituent or substituents and in said arylcarbonyloxy groups which may have a substituent or substituents includes, for example, phenyl, naphthyl, thienyl and furyl. The aralkyl group in said aralkyl groups which may have a substituent or substituents and in said aralkylcarbonyloxy groups which may have a substituent or substituents includes, for example, benzyl and phenethyl. The substituent for such aryl group or aralkyl groups includes, for example, lower alkyl of 1 to 5 carbon atoms (e.g., methyl, ethyl, n-propyl, isopropyl, n-butyl, sec-butyl, tert-butyl, n-pentyl, etc.), lower alkoxy of 1 to 3 carbon atoms (e.g., methoxy, ethoxy, propoxy, etc.), halogen (e.g., chlorine, bromine, iodine, fluorine, etc.), nitro, amino, oxo, hydroxyl and benzyloxy.

The alkenyl group in the above alkenyl groups having a molecular weight of from 58 to 400 which may have a substituent or substituents is preferably those having 2 to 20 carbon atoms, and examples of such alkenyl groups include, for example, vinyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl and eicosenyl, with the substituent for such alkenyl groups including for example aryl groups (e.g., phenyl, naphthyl, etc.) aralkyl (e.g. benzyl, phenethyl, etc.) and 5- or 6-membered heterocyclic groups (e.g., 3-pyridyl, thienyl, furyl, etc.).

The aryl group in the above aryl groups having a molecular weight of from 58 to 400 which may have a substituent or substituents includes, for example, phenyl and naphthyl. The substituent for such aryl groups includes, for example, alkyl groups of 1 to 5 carbon atoms (e.g., methyl, ethyl, n-propyl, isopropyl, n-butyl, isobutyl, sec-butyl, tert-butyl, n-pentyl, etc.), and methoxy, methylenedioxy and hydroxyl groups.

The aralkyl group in the above aralkyl groups having a molecular weight of from 58 to 400 which may have a substituent or substituents includes, for example, benzyl and phenethyl. The substituent for such aralkyl groups includes, for example, alkyl groups of 1 to 5 carbon atoms (e.g., methyl, ethyl, n-propyl, isopropyl, n-butyl, isobutyl, sec-butyl, tert-butyl, n-pentyl, etc.), and methoxy, methylenedioxy and hydroxyl groups.

The acyl group in the above acyl groups having a molecular weight of from 58 to 400 which may have a substituent or substituents is preferably those having 1 to 9 carbon atoms, and examples of such acyl groups include, for example, formyl, acetyl, propionyl, butyryl, isobutyryl, benzoyl, morpholinocarbonyl, $C_{1-3}$alkoxycarbonylpyrrolidinocarbonyl (e.g., 2-methoxycarbonylpyrrolidinocarbonyl, 2-propoxycarbonylpyrrolidinocarbonyl, etc.), $C_{1-3}$alkoxycarbonyl (e.g., methoxycarbonyl, ethoxycarbonyl, propoxycarbonyl, etc.), arylcarbonyl which may have a substituent or substituents and aralkylcarbonyl which may have a substituent or substituents.

The aryl in the above arylcarbonyl which may have a substituent or substituents includes, for example, phenyl and naphthyl. The aralkyl in the above aralkylcarbonyl which may have a substituent or substituents includes, for example, benzyl and phenethyl. The substituent for such aryl or aralkyl includes, for example, hydroxyl, lower alkyl of 1 to 5 carbon atoms (e.g., methyl, ethyl, n-propyl, isopropyl, n-butyl, isobutyl, tert-butyl, n-pentyl, etc.) and lower alkoxy of 1 to 3 carbon atoms (e.g., methoxy, ethoxy, propoxy, etc.).

The aryl in the above aryloxy groups having a molecular weight of from 58 to 400 which may have a substituent or substituents includes, for example, phenyl, naphthyl, thienyl and furyl, and examples of the substituent include, for example, hydroxyl group, lower alkyl of 1 to 5 carbon atoms (e.g., methyl, ethyl, n-propyl, isopropyl, n-butyl, sec-butyl, tert-butyl, n-pentyl, etc.) and lower alkoxy of 1 to 3 carbon atoms (e.g., methoxy, ethoxy, propoxy, etc.).

The aralkyl in the above aralkyloxy groups having a molecular weight of from 58 to 400 which may have a substituent or substituents includes, for example, benzyl and phenethyl, and examples of the substituent include, for example, hydroxyl group, lower alkyl of 1 to 5 carbon atoms (e.g., methyl, ethyl, n-propyl, isopropyl, n-butyl, sec-butyl, tert-butyl, n-pentyl, etc.) and lower alkoxy of 1 to 3 carbon atoms (e.g., methoxy, ethoxy, propoxy, etc.).

As the number of said substituents, one to three is preferable.

In the above formulae, the group removable by a hydrolysis or reduction reaction as represented by $R_2$ includes, for example, methoxymethyl, benzyloxymethyl, 2-tetrahydropyranyl, trimethylsilyl, dimethyl-tert-butylsilyl, benzyl and p-methoxybenzyl.

The above acetal includes, for example, groups of the formula:

(wherein $R_3$ is hydrogen, methyl, phenyl, p-methoxyphenyl, etc.), and the ketal includes, for example, groups of the formula:

(wherein $R_4$ and $R_5$ are the same or different, and each represents hydrogen atom, methyl or ethyl or $R_4$ and $R_5$ jointly form $-(CH_2)_a-$, wherein a is 4 or 5).

The compounds [I] of the present invention are produced by subjecting the compound [II] to a hydrolysis reaction and/or a reduction reaction.

In the case of a compound [II] wherein the protective group $R_2$ at the 3-position is a group (e.g., methoxymethyl, benzyloxymethyl, trimethylsilyl, dimethyl-tert-butylsilyl) removable by a hydrolysis reaction, particularly, the elimination of the protective group at the 3-position and the removal of the acetal or ketal group at the 5- and 6-positions can be carried out simultaneously by subjecting the compound [II] to a hydrolysis reaction to give the compound [I].

In the case of a compound [II] wherein the protective group $R_2$ at the 3-position is a group (e.g., 2-tetrahydropyranyl, benzyl, p-methoxybenzyl) removable by a reduction reaction, the acetal or ketal group at the 5- and 6-positions is removed firstly by subjecting the compound [II] to a hydrolysis reaction to give the compound [III], and then, the protective group can be removed by subjecting it to a reduction reaction to yield the compound [I].

The above hydrolysis reaction is carried out by contacting a starting compound with an acid catalyst. The said acid catalyst includes, for example, hydrochloric acid, sulfuric acid, p-toluenesulfonic acid, perchloric acid and acetic acid. This reaction is conducted in an aqueous solvent, and the said solvent includes, for example, methanol, ethanol, dioxane, 1,2-methoxyethane and tetrahydrofuran. The reaction temperature is selected from the range of about 0° C. to 80° C. The reaction time is about 10 minutes to 3 hours.

The above reduction reaction includes, for example, catalytic reduction. The said catalytic reduction is carried out by contacting a starting compound with a catalyst. The said catalyst includes, for example, palladium, palladiumcarbon, platinum black and platinum dioxide. This reaction is normally carried out in a solvent. The said solvent includes, for example, methanol, ethanol, acetic acid and ethyl acetate. The reaction temperature is about 10° C. to 40° C., while the reaction time is about 1 to 18 hours.

The ascorbic acid derivative [I] thus produced can be separated and collected by per se known separation and purification means (e.g., column chromatography using polystyrene resins, activated carbon, reverse phase system, etc., recrystallization, etc.).

The compound [II] which is used as a starting material in the process of the present invention can be produced, for example, by the reaction steps to be shown below.

In the above formulae, X is an acetal or ketal residue.

The above reaction involving the acetalization or ketalization of ascorbic acid to produce the compound [V] is carried out by reacting ascorbic acid with a ketone or aldehyde, such as acetone, benzaldehyde, cyclopentanone and cyclohexanone. As the reaction solvent, there are used, for example, tetrahydrofuran, chloroform, diethyl ether, dichloromethane and dichloroethane. The reaction temperature is room temperature to 60° C., whereby the reaction is carried out in the presence of an acid catalyst. The catalyst includes, for example, sulfuric acid, p-toluenesulfonic acid and camphorsulfonic acid. The reaction time is 4 to 24 hours.

Subsequently, the compound [V] is reacted with a compound (e.g., chloromethyl methyl ether, benzyl chloride, benzyl bromide, etc.) of the formula $R_2$—Y [wherein $R_2$ is as defined hereinbefore; Y is halogen (e.g., chlorine, bromine, etc.)] in dimethylformamide, dimethylsulfoxide, hexamethylphosphoramide or tetrahydrofuran, either singly or a solvent mixture thereof in the presence of an inorganic base, such as potassium carbonate, sodium carbonate, sodium hydroxide, potassium hydroxide and sodium hydrogencarbonate to produce the compound [IV]. The reaction is carried out at a reaction temperature of 0° C. to 40° C. (preferably 25° C.), and goes to conclusion within 1 to 18 hours.

Then, the compound [IV] thus obtained is reacted with a compound of the formula $R_1$—$CH_2$—Z [wherein $R_1$ is as defined hereinbefore; Z is halogen (e.g., chlorine, bromine, etc.)] in a solvent such as dimethylformamide, dimethylsulfoxide, hexamethylphosphoramide and tetrahydrofuran, solely or as a solvent mixture thereof, in the presence of an inorganic base (e.g., sodium hydroxide, potassium hydroxide, sodium carbonate, potassium carbonate, etc.) at a temperature of 10° to 60° C. for 1 to 18 hours to produce the compound [II].

The compound [II] or [III] as produced in accordance with the process of the present invention is useful, for example, as a synthesis intermediate in the production of the compound [I].

The compound [I], which possesses oxidation inhibitory activity and also exhibits an $LD_{50}$ value of 0.8 to 10 g/kg when given orally to mice, thus being of low toxicity, can be used as an antioxidant for food.

The utilization of the compound [I] as an antioxidant for food is conducted by forming it into an antioxidant preparation for food containing the compound [I], followed by addition to, or contacting with, a food product.

In processing or formulating into a preparation, for example, the compound [I] may be formed, without being diluted, by per se known methods, or may be formed after being diluted.

In the case of dilution, for example, a carrier (e.g., lactose, starch, etc.) is admixed with the compound [I], and the mixture is formed into powders or granules by per se known methods.

The foods, to which the antioxidant preparation for food according to the present invention is to be added, include, for example, fruit juice, fruits, edible meat products, fishes and shellfishes, and oils and fats (e.g., salad oil, lard oil, etc.).

As the method of using the antioxidant preparation for food according to the present invention, when the compound [I], the active ingredient thereof, is soluble in water, there may be mentioned, for example, a method which comprises adding for dissolution the powdered antioxidant preparation for food according to the present invention directly to foods, such as fruit juice, fruits and edible meat products, or a method which comprises dissolving the antioxidant preparation for food according to the present invention in advance in water and adding the resulting solution to fruit juice, fruits or edible meat products or immersing fishes and shellfishes in the said solution.

The antioxidant preparation for food according to the present invention, in cases in which it is used in edible meat products and fishes and shellfishes, can be brought into an aqueous emulsion thereof with use of an emulsifying agent to thereby put into use.

When the compound [I], the active ingredient, is soluble in oil, the antioxidant preparation for food according to the present invention is added directly to oils and fats.

The used amount of the antioxidant preparation for food according to the present invention, as the compound [I], is for example about 0.02 to 0.04% (W/W) in the case of fruit juice and fruits, about 0.02 to 0.08% (W/W) in the case of edible meat products, about 0.02 to 0.08% (W/W) in the case of it being blended into fishes and shellfishes, about 0.1 to 1% (W/W) as the concentration of a solution to be prepared in the case of immersion, and about 0.002 to 0.02% (W/W) in the case of oils and fats.

Further, the compound [I] may be also used as a bleaching beauty agent for cosmetics. The used amount of the present compound [I] in the bleaching beauty agent for cosmetics, as the compound [I], is for example about 0.1 to 1% (W/V) in the case of lotion, and about 0.1 to 1% (W/W) in the case of cream.

The experiment examples, reference examples and examples are described below to illustrate the present invention more specifically.

EXPERIMENT 1

Oxidation inhibitory activity determined with use of a stable radical:

In accordance with the method of Brois MS [Nature, 181, 1199, 1958], the reduction activity of $\alpha,\alpha$-diphenyl-$\beta$-picrylhydrazyl (DPPH) was determined, which is used as a scale of rating the oxidation inhibition activity. Thus, a test chemical compound [i.e., the compound [I] wherein $R_1=-(CH_2)_{16}CH_3$] was added to 3 ml of 0.1 mM DPPH ethanol solution, and 20 minutes later, the absorbance was measured at a wavelength of 517 nm with use of a spectrophotometer, whereby the difference in absorbance from the solvent (not more than 0.5% of DMF) reference was taken as the reduction activity.

Figure 1:
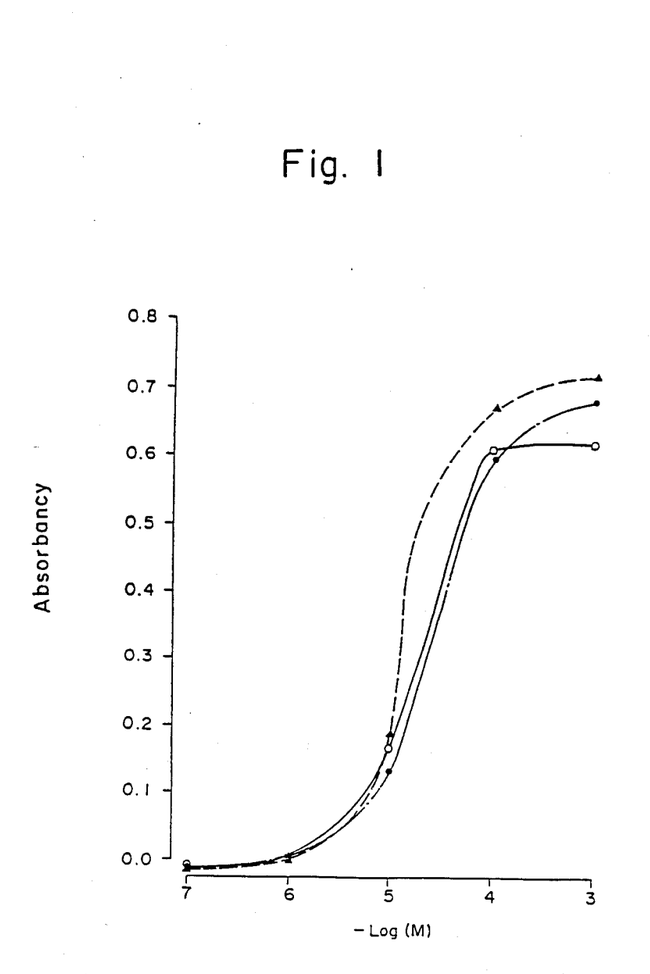

The results of the experiment are as shown in FIG. 1.

In FIG. 1, ● indicates the results with the above test chemical compound, ○ the results with vitamin E, and ▲ the results with vitamin C.

The above test chemical compound was found to reduce DPPH at the concentration of not less than $10^{-5}$M in a manner dependent upon the amount used. Vitamins C and E showed the activity equal to that of the test chemical compound.

EXPERIMENT 2

Sardine, after having removed the internals and bones, was minced, and the mince meat was formed without addition of, and with addition at a rate of 0.03% and 0.05% of, the compound [I] wherein $R_1=(CH_2)_4CH_3$ to prepare meatballs. The meatballs were preserved by freezing at $-20°$ C., and the peroxide value (POV) was measured with relation to a length of time elapsed. The results are shown in Table 1.

TABLE 1

| Added amount | No. of days preserved | | | |
|---|---|---|---|---|
| | 0 | 30 | 60 | 90 |
| — | 6.9 | 34.5 | 54.1 | 70.3 |
| 0.03% | 6.9 | 10.3 | 15.6 | 30.5 |
| 0.05% | 6.9 | 7.5 | 10.4 | 28.7 |

EXPERIMENT 3

In a Petri dish of a diameter of about 10 cm was placed 25 g of salad oil, which was preserved in a thermostat at 60° C. without addition of, and with addition for dissolution at a rate of 0.03% and 0.05% of, the compound [I] wherein $R_1=(CH_2)_{16}CH_3$, and the peroxide value (POV) was measured with relation to a length of time elapsed. The results are shown in Table 2.

TABLE 2

| Added amount | No. of days preserved | | | |
|---|---|---|---|---|
| | 0 | 30 | 60 | 90 |
| — | 2.3 | 10 | 57 | 83 |
| 0.03% | 2.3 | 5 | 34 | 51 |
| 0.05% | 2.3 | 4 | 29 | 45 |

REFERENCE EXAMPLE 1

(1) L-ascorbic acid acetonide (21.6 g, 0.1 mole) was dissolved in dimethylformamide (210 ml), and the solution was cooled with ice. To the solution were added potassium carbonate (14 g, 0.1 mole) and successively benzyl bromide (11.2 ml), followed by stirring at room temperature for 20 hours. After the conclusion of the reaction, water (100 ml) was added to the reaction solution, and the mixture was neutralized with 2N hydrochloric acid to adjust to pH 5.0, followed by extraction with two portions of ethyl acetate. The organic layer was washed with water, dried (over magnesium sulfate) and then concentrated under reduced pressure. The product was subjected to silica gel column chromatography, and elution was effected with isopropyl ether-ethyl acetate (3:1). The eluate was concentrated, and then the residue was recrystallized from isopropyl ether-ethyl acetate to give L-5,6-O,O-isopropylidene-3-O-benzylascorbic acid (13 g, 40%), m.p. 105°–106° C.

(2) L-5,6-O,O-isopropylidene-3-O-benzylascorbic acid (3.06 g, 0.01 mole) was dissolved in a solvent mixture of dimethylsulfoxide (20 ml) and tetrahydrofuran (15 ml), and potassium carbonate (1.5 g, 0.011 mole) was added to the solution. Then, octadecyl iodide (3.83 g) was added to the mixture, followed by stirring at room temperature for 18 hours. After the conclusion of the reaction, water (100 ml) was added to the reaction mixture, followed by extraction with ethyl acetate. The organic layer was washed with water, dried (over magnesium sulfate) and then concentrated under reduced pressure. The residue was subjected to silica-gel column chromatography, followed by elution with isopropyl ether-ethyl acetate (10:1) to give L-5,6-O,O-isopropylidene-3-O-benzyl-2-O-octadecylascorbic acid (3.8 g). m.p. 44°–45° C.

Nuclear magnetic resonance spectrum. (CDCl$_3$, internal standard: TMS, $\delta$value). 7.29(5H, s), 5.43(2H, s), 4.51(1H, d, 2 Hz), 4.08(3H, m), 1.38 (6H, s), 1.26(32H, m), 0.88(3H, t).

REFERENCE EXAMPLE 2

(1) L-Ascorbic acid acetonide (42 g, 0.19 mole) was dissolved in a solvent mixture of dimethylformamide (100 ml) and hexamethylphosphoramide (100 ml), and potassium carbonate (32 g, 0.23 mole) was added to the solution, followed by ice-cooling. A solution of chloromethyl methyl ether (18 g, 0.22 mole) in tetrahydrofuran (25 ml) was added dropwise to the mixture over the 20 minutes period. After stirring at room temperature for 2.5 hours, water (100 ml) was added to the reaction mixture, to which 2N hydrochloric acid was added to adjust to pH 5.0, followed by extraction with four portions of ethyl acetate. The organic layer was washed with water, dried and then concentrated under reduced pressure, and the residue was subjected to silica gel column chromatography, followed by elution with isopropyl ether-ethyl acetate (2:1). The eluate was concentrated, and the residue was recrystallized from the same solvent system to give L-5,6-O,O-isopropylidene-3-O-methoxymethylascorbic acid (46 g). m.p. 93°–94° C.

Elemental analysis, for $C_{11}H_{16}O_7$. Found: C, 50.84; H, 6.05. Calcd.: C, 50.77; H, 6.20.

(2) L-5,6-O,O-isopropylidene-3-O-methoxymethylascorbic acid (1.84 g, 7.1 mmole) was dissolved in dimethylsulfoxide (10 ml), and octadecyl iodide (10 ml) and potassium carbonate (1.0 g) were added to the solution, followed by allowing the reaction to proceed at 60° C. for 6 hours. After the conclusion of the reaction, water (50 ml) was added to the reaction mixture, followed by extraction of the reaction product with ethyl acetate. The organic layer was washed with water, dried and concentrated under reduced pressure, and the residue was subjected to silica gel column chromatography, followed by elution with isopropyl ether. The eluate was concentrated, and the residue was recrystallized from isopropyl ether-ethyl acetate to give L-5,6-O,O-isopropylidene-3-O-methoxymethyl-2-O-octadecylascorbic acid (0.8 g), m.p. 50° to 52° C.

Nuclear magnetic resonance spectrum. (CDCl$_3$, internal standard: TMS*, δvalue). 5.42(2H, s), 4.53(1H, d, 2 Hz), 4.10(5H, m), 3.51 (3H, s), 1.38 (3H, s), 1.36(3H, s), 1.27(32H, m), 0.88(3H, t).

*TMS: Tetramethylsilane

REFERENCE EXAMPLE 3

By the same procedure as in Reference Example 1 or 2, there were obtained the compounds (represented by the formula [II] wherein $R_1$ and $R_2$ are as specified in the below Table) as shown in the below Table.

| Compound No. | Reference Example No. which is referred to | $R_1$ | $R_2$ | melting point °C. | magnetic resonance spectrum (CDCl$_3$, internal standard TMS, δ value) |
|---|---|---|---|---|---|
| Ref. Ex. 3-1 | 2 | —(CH$_2$)$_4$CH$_3$ | —CH$_2$OCH$_3$ | oil | 5.40(2H, s), 4.51(2H, d, 2Hz), 4.09(5H, m), 3.50 (3H, s), 1.36(14H, m), 0.87(3H, t) |
| Ref. Ex. 3-2 | 1 | —(CH$_2$)$_6$CH$_3$ |  | oil | 7.36(5H, s), 5.46(2H, s), 4.54(1H, d, 2Hz), 4.06 (5H, m), 1.37(3H, s), 1.34(3H, s), 1.27(12H, m), 0.87(3H, t) |
| Ref. Ex. 3-3 | 1 | —(CH$_2$)$_8$CH$_3$ |  | oil | 7.37(5H, s), 5.46(2H, s), 4.54(1H, d, 2Hz), 4.08 (5H, m), 1.37(3H, s), 1.34(3H, s), 1.26(16H, m), 0.86(3H, t) |
| Ref. Ex. 3-4 | 1 | —(CH$_2$)$_{15}$CH$_3$ |  | oil | 7.36(5H, s), 5.46(2H, s), 4.54(1H, d, 2Hz), 4.08 (5H, m), 1.37(3H, s), 1.34(3H, s), 1.25(30H, m), 0.87(3H, t) |
| Ref. Ex. 3-5 | 1 | —(CH$_2$)$_{18}$CH$_3$ |  | 48–50 | 7.36(5H, s), 5.46(2H, s), 4.54(1H, d, 2Hz), 4.06 (5H, m), 1.37(3H, s), 1.34(3H, s), 1.24(36H, m), 0.87(3H, t) |
| Ref. Ex. 3-6 | 1 | —(CH$_2$)$_{20}$CH$_3$ |  | 60–61 | 7.36(5H, s), 5.45(2H, s), 4.53(1H, d, 2Hz), 4.06 (5H, m), 1.37(3H, s), 1.34(3H, s), 1.24(40H, m), 0.87(3H, t) |
| Ref. Ex. 3-7 | 2 |  | —(CH$_2$OCH$_3$) | oil | 7.20(5H, s), 5.17(2H, s), 5.05(2H, s), 1.37(3H, s), 4.50(1H, d, 2Hz), 4.06 (3H, m), 3.38(3H, s), 1.34(3H, s) |
| Ref. Ex. 3-8 | 1 |  |  | 148–149 | 7.30(5H, s), 5.67(2H, s), 4.81(2H, m), 4.55 (2H, m), 4.10(3H, m), 3.65(8H, m), 1.37(6H, s) |
| Ref. Ex. 3-9 | 2 |  | —CH$_2$OCH$_3$ | oil | 7.34(5H, s), 5.79(1H, d, 11Hz), 5.67(1H, d, 11Hz), 4.53(3H, m), 4.23(1H, m), 4.02(3H, m), 3.60(3H, s), 3.49(2H, m), 2.04(4H, m), 1.36(3H, s), 1.32(3H, s) |

-continued

| Compound No. | Reference Example No. which is referred to | R₁ | R₂ | melting point °C. | magnetic resonance spectrum (CDCl₃, internal standard TMS, δ value) |
|---|---|---|---|---|---|
| Ref. Ex. 3-10 | 2 |  | —CH₂OCH₃ | oil | 7.45(7H, m), 5.57(2H, s), 5.08(2H, s), 4.51(1H, d, 2Hz), 3.07(3H, m), 3.36 (3H, s), 1.44(3H, s), 1.36 (3H, s) |
| Ref. Ex. 3-11 | 2 |  | —CH₂OCH₃ | oil | 5.42(2H, s), 5.31(2H, m), 4.57(1H, d, 2Hz), 4.10(5H, m), 3.51(3H, s), 2.00(4H, m), 1.37(3H, s), 1.36(3H, s), 1.30(20H, m), 0.88(3H, t) |
| Ref. Ex. 3-12 | 2 | —COOCH₃ | —CH₂OCH₃ | oil | 5.62(1H, d, 2Hz), 5.49(1H, d, 2Hz), 4.75(2H, s), 4.54 (1H, d, 2Hz), 4.12(3H, m), 3.74(3H, s), 3.52(3H, s), 1.37(6H, s) |
| Ref. Ex. 3-13 | 2 | —(CH₂)₃COOCH₃ | —CH₂OCH₃ | oil | 5.36(2H, s), 4.51(1H, d, 2Hz), 4.10(5H, m), 3.65 (3H, s), 3.49(3H, s), 2.35 (2H, m), 1.72(4H, m), 1.37 (6H, s) |
| Ref. Ex. 3-14 | 1 | —(CH₂)₉COOCH₃ |  | oil | 7.26(5H, s), 5.42(2H, s), 4.48(1H, d, 2Hz), 4.06(5H, m), 3.63(3H, s), 2.27(2H, m), 1.36(24H, m) |
| Ref. Ex. 3-15 | 1 |  |  | oil | 7.30(15H, m), 4.95(2H, s), 4.88(2H, s), 4.81(2H, s), 4.51(1H, m), 4.12(3H, m), 1.35(3H, s), 2.14(3H, s), 1.27(16H, m), 1.37(3H, s) |
| Ref. Ex. 3-16 | 2 |  | —CH₂OCH₃ | oil | 8.50(1H, m), 7.38(7H, m), 6.11(1H, t, 7Hz), 5.40(2H, s), 4.55(1H, m), 4.18(7H, m), 3.48(3H, s), 2.18(2H, m), 1.66(6H, m), 1.38(3H, s), 1.36(3H, s), 8.42(1H, m) |
| Ref. Ex. 3-17 | 1 | —(CH₂)₁₃CH₃ |  | oil | 7.36(5H, s), 5.46(2H, s), 4.53(1H, d, 2Hz), 4.08(5H, m), 1.37(3H, s), 1.34(3H, m), 1.26(26H, m), 0.86(3H, t) |
| Ref. Ex. 3-18 | 2 | —(CH₂)₉—COOCH₃ | —CH₂—OCH₃ | Oil | 5.39(2H, s), 4.51(1H, m) 4.12(3H, m), 3.64(3H, s) 3.49(3H, s), 2.28(2H, m) 1.37(3H, s), 1.35(3H, m) 1.28(16H, m) |
| Ref. Ex. 3-19 | 2 | —(CH₂)₁₀CH₃ | —CH₂OCH₃ | Oil | 5.40(2H, s), 4.55(1H, d, 2Hz), 4.08(5H, m), 3.47(3H, s), 1.37(3H, s) 1.33(3H, s), 1.24(20H, m), 0.86(3H, t) |

-continued

| Compound No. | Reference Example No. which is referred to | R₁ | R₂ | melting point °C. | magnetic resonance spectrum (CDCl₃, internal standard TMS, δ value) |
|---|---|---|---|---|---|
| Ref. Ex. 3-20 | 1 | —(CH₂)₁₂CH₃ | —CH₂—C₆H₅ | Oil | 7.36(5H, s), 5.46(2H, s), 4.54(1H, d, 2Hz), 4.07(5H, m), 1.37(3H, s), 1.34(3H, s), 1.24(24H, m), 0.86(3H, t) |
| Ref. Ex. 3-21 | 1 | —(CH₂)₁₄CH₃ | —CH₂—C₆H₅ | Oil | 7.37(5H, s), 5.46(2H, s) 4.54(1H, d, 2Hz), 4.06(5H, m), 1.37(3H, s), 1.34(3H, s), 1.25(28H, m), 0.85(3H, t) |

EXAMPLE 1

L-5,6-O,O-Isopropylidene-3-O-methoxymethyl-2-O-octadecylascorbic acid (1.2 g) was dissolved in a solvent mixture of methanol (30 ml) and tetrahydrofuran (10 ml), and 2N hydrochloric acid (10 ml) was added to the solution, followed by stirring at 50° C. for 6 hours. The reaction solution was concentrated under reduced pressure, and the reaction product was extracted with ethyl acetate. The organic layer was washed with water, dried (over magnesium sulfate) and then concentrated under reduced pressure, and the residue was recrystallized from isopropyl ether-ethyl acetate to give 2-O-octadecylascorbic acid (0.82 g). m.p. 127°–128° C.

Nuclear magnetic resonance spectrum. (CDCl₃, internal standard: TMS, δvalue). 4.69(1H, d), 3.88(3H, m), 3.53(2H, m), 1.25(32H, m), 0.87(3H, t).

EXAMPLE 2

L-5,6-O,O-Isopropylidene-3-O-benzyl-2-O-octadecylascorbic acid (3.8 g) was dissolved in a solvent mixture of tetrahydrofuran (40 ml) and methanol (10 ml), and 2N hydrochloric acid (20 ml) was added to the solution, followed by stirring at 50° C. for 24 hours. After the conclusion of the reaction, the reaction solution was concentrated under reduced pressure, and the reaction product was extracted with ethyl acetate. The organic layer was washed with water, dried and then concentrated under reduced pressure, and the residue was recrystallized from isopropyl ether-ethyl acetate to give 3-O-benzyl-2-O-octadecylascorbic acid (2.6 g). m.p. 75°–76° C.

Nuclear magnetic resonance spectrum. (CDCl₃, internal standard: TMS, δvalue). 7.32(5H, s), 5.45(2H, s), 4.66(1H, d), 4.00(5H, m), 1.26(32H, m), 0.87(3H, t).

EXAMPLE 3

By the same procedure as in Example 2, there were obtained the compounds as shown below. In the below Table, the obtained examples show the structural formulae as represented by the above formula [III].

| Compound No. | R₁ | R₂ | melting point °C. | magnetic resonance spectrum (CDCl₃ internal standard TMS, δ value) |
|---|---|---|---|---|
| 3-1 | —(CH₂)₆CH₃ | —CH₂—C₆H₅ | oil | 7.34(5H,s),5.45(2H, s),4.67(1H,m),3.97 (4H,m),3.77(2H,m), 1.24(12H,m),0.86(3H,t) |
| 3-2 | —(CH₂)₈CH₃ | —CH₂—C₆H₅ | oil | 7.36(5H,s),5.46(2H,s) 4.68(1H,m),4.00(3H,m), 3.80(2H,m),1.25(16H,m), 0.86(3H,t) |
| 3-3 | —(CH₂)₁₃CH₃ | —CH₂—C₆H₅ | 62–63° C. | 7.36(5H,s),5.47(2H,s), 4.68(1H,m),4.02(3H,m), 3.82(2H,m),1.23(26H,m), 0.87(3H,t) |
| 3-4 | —(CH₂)₁₅CH₃ | —CH₂—C₆H₅ | 57–58° C. | 7.33(5H,s),5.44(2H,s), 4.67(1H,m),4.00(3H,m), 3.79(2H,m),1.25(30H,m), 0.88(3H,t) |
| 3-5 | —(CH₂)₁₈CH₃ | —CH₂—C₆H₅ | 77–78° C. | 7.36(5H,s),5.46(2H,s), 4.68(1H,m),4.00(3H,m), 3.82(2H,m),1.24(36H,m), 0.86(3H,t) |

| Compound No. | R₁ | R₂ | melting point °C. | magnetic resonance spectrum (CDCl₃ internal standared TMS, δ value) |
|---|---|---|---|---|
| 3-6 | —(CH₂)₂₀CH₃ | —CH₂—C₆H₅ | 83–85° C. | 7.36(5H,s),5.46(2H,s), 4.69(1H,m),4.02(4H,m), 3.82(2H,m),1.25(40H,m), 0.86(3H,t) |
| 3-7 | (nonyl-substituted tetramethoxy/dibenzyloxy aromatic, —(CH₂)₉–Ar with CH₃, OCH₃, OCH₃, OCH₂Ph, OCH₂Ph) | —CH₂—C₆H₅ | Oil | 1.40(16H,m),2.13(3H,s), 2.23(2H,s),3.91(6H,s), 4.06(5H,m),4.90(2H,s), 4.97(2H,s),5.57(2H,m), 7.30(15H,m) |
| 3-8 | —CO—N(morpholino) | —CH₂—C₆H₅ | Oil | 3.37(4H,m),3.49(4H,m), 3.90(2H,m),4.20(1H,m), 4.79(2H,s),4.89(1H,d), 5.56(1H,d),5.75(1H,d), 7.40(5H,s) |
| 3-9 | —(CH₂)₁₂CH₃ | —CH₂—C₆H₅ | 60–61° C. | 7.35(5H,s),5.47(2H,s), 4.68(1H,m),4.00(3H,m), 3.80(2H,m),1.26(24H,m), 0.86(3H,t) |
| 3-10 | —(CH₂)₁₄CH₃ | —CH₂—C₆H₅ | 71–72° C. | 7.37(5H,s),5.47(2H,s), 4.69(1H,m),4.02(3H,m), 3.85(2H,m),1.25(28H,m), 0.86(3H,t) |

EXAMPLE 4

3-O-Benzyl-2-O-octadecylascorbic acid (2.1 g) was dissolved in ethyl acetate (25 ml), and 5% Pd-C (0.5 g) was added to the solution to conduct catalytic reduction at atmospheric pressure. The catalyst was filtered out, and the filtrate was concentrated under reduced pressure. The reaction product was recrystallized from isopropyl ether-ethyl acetate to give 2-O-octadecylascorbic acid (1.5 g). m.p. 127°–128° C.

NMR spectrum (d₆-DMSO): 4.69(1H, d), 3.88(3H, m), 3.53(2H, m), 1.25(32H, m), 0.87(3H, t).

EXAMPLE 5

By the same procedure as in Example 1 or 4, the compounds as shown below were obtained. In the following Table, the obtained compounds show the structural formulae as represented by the above formula [I].

The compounds (4 through 15) were obtained by carrying out the same methods as in Examples 2 and 3 and oxidizing the resulting hydroquinone derivatives with ferric chloride.

| Compound No. | Example No. to which referred | R₁ | melting point °C. | NMR specutrum (d₆-DMSO, internal standared: TMS, δ value) |
|---|---|---|---|---|
| 5-1 | 1 | —(CH₂)₄CH₃ | 100–101 | 4.70(1H,d,2Hz),3.89(3H, m),3.54(2H,m),1.32(8H,m), 0.88(3H,t) |
| 5-2 | 2,4 | —(CH₂)₆CH₃ | 115–117 | 4.70(1H,d,2Hz),3.85(3H, m),3.53(2H,m),1.26(12H, m),0.84(3H,t) |
| 5-3 | 2,4 | —(CH₂)₈CH₃ | 118–120 | 4.71(1H,d,2Hz),3.85(3H, m),3.54(2H,m),1.27(16H, m),0.85(3H,t) |
| 5-4 | 2,4 | —(CH₂)₁₅CH₃ | 127–129 | 4.71(1H,d,2Hz),3.86(3H, m),3.54(2H,m),1.27(30H, m),0.86(3H,t) |
| 5-5 | 2,4 | —(CH₂)₁₈CH₃ | 126–127 | 4.70(1H,s),3.86(3H,m), 3.45(2H,m),1.23(36H,m), 0.85(3H,t) |

-continued

| Compound No. | Example No. to which referred | $R_1$ | melting point °C. | NMR spectrum (d$_6$-DMSO, internal standard: TMS, δ value) |
|---|---|---|---|---|
| 5-6 | 2,4 | —(CH$_2$)$_{20}$CH$_3$ | 125–127 | 4.70(1H,s),3.86(3H,m), 3.46(2H,m),1.24(40H,m), 0.86(3H,t) |
| 5-7 | 1 | —C$_6$H$_5$ (phenyl) | 126–127 | 7.33(5H,m),6.65(OH), 5.00(2H,s),4.73(1H,s), 3.59(3H,m) |
| 5-8 | 2,4 | —C(=O)—N(morpholino) | Oil | 4.64(1H,d,2Hz),4.56(2H, s),4.40(1H,m),3.56(11H, m) |
| 5-9 | 1 | —C(=O)—N(pyrrolidinyl-2-COOCH$_3$) | Oil | 4.74(1H,s),4.60(2H,s), 4.35(3H,m),3.62(3H,s), 3.44(5H,m),1.95(4H,m) |
| 5-10 | 1 | naphthyl | Oil | 7.45(7H,m),5.40(2H,s), 4.74(1H,d,2Hz),3.66(5H, m) |
| 5-11 | 1 | —(CH$_2$)$_7$—CH=CH—(CH$_2$)$_7$CH$_3$ | 101–104 | 5.21(2H,t,6Hz),4.69(1H, d,2Hz),2.80(5H,m),1.98 (4H,m),1.25(20H,m),0.86 (3H,t) |
| 5-12 | 1 | —COOCH$_3$ | Oil | 4.73(1H,d,2Hz),4.59(2H, s),3.71(3H,s),3.54(3H,m) |
| 5-13 | 1 | —(CH$_2$)$_3$COOCH$_3$ | Oil | 4.67(1H,d,2Hz),3.88(5H, m),3.65(3H,s),2.35(2H,m), 1.70(4H,m) |
| 5-14 | 2,4 | —(CH$_2$)$_9$COOCH$_3$ | 78–80 | 4.72(1H,d,2Hz),3.95(3H, m),3.63(3H,s),2.27(2H,m), 1.30(16H,m) |
| 5-15 | 2,4 | —(CH$_2$)$_9$-(2,3-dimethoxy-5-methyl-1,4-benzoquinonyl) | Oil | 3.85(6H,s),3.90(5H,m), 2.57(2H,m),2.12(3H,s), 1.27(16H,m) |
| 5-16 | 1 | —(CH$_2$)$_4$—CH=C(phenyl)(3-pyridyl) | Oil | 8.45(2H,m),7.38(7H,m), 6.10(1H,t,7Hz),4.63(1H, m),3.80(5H,m),2.10(2H,m), 1.46(6H,m) |
| 5-17 | 2,4 | —(CH$_2$)$_{13}$CH$_3$ | 126–127 | 4.74(1H,s),3.85(3H,m), 3.44(2H,m),1.24(26H,m), 0.84(3H,t) |
| 5-18 | 1 | —(CH$_2$)$_{10}$CH$_3$ | 127–128 | 4.72(1H,s),3.91(3H,m), 3.53(2H,m),1.24(18H,m), 0.85(3H,t) |
| 5-19 | 2,4 | —(CH$_2$)$_{12}$CH$_3$ | 126–127 | 4.74(1H,s),3.90(3H,m), 3.51(2H,m),1.25(24H,m), 0.85(3H,t) |
| 5-20 | 2,4 | —(CH$_2$)$_{14}$CH$_3$ | 128–129 | 4.75(1H,s),3.94(3H,m), |

| Compound No. | Example No. to which referred | $R_1$ | melting point °C. | NMR specutrum ($d_6$-DMSO, internal standared: TMS, δ value) |
| --- | --- | --- | --- | --- |
| | | | | 3.59(2H,m),1.24(28H,m), 0.86(3H,t) |

EXAMPLE 6

In a microspeed mixer (manufactured by Takara Koki Co., Ltd., Japan) were mixed for about 2 minutes 1.5 kg of the compound of the formula [I] wherein $R_1 = -COOCH_3$ as obtained in example 5-12, 1.5 kg of carrageenin and 1.5 kg of dextrin to reduce the mixture to powder.

Mackerel was immersed in a solution of 15 g of the above powder in 1 l of water for 10 seconds, drawn off of water and preserved at $-20°$ C. for 6 months. This product was less rancid and had better color and gloss, as compared with the non-treated control section.

EXAMPLE 7

In a microspeed mixer (manufactured by Takara Koki Co., Ltd., Japan) were mixed for about 2 minutes 3 kg of the compound of the formula [I] wherein $R_1 = COOCH_3$ as obtained in Example 5-12 and 2 kg of dextrin to produce a powder.

The pickles were prepared by adding for dissolution to 8.2 kg of ice-cold water 900 g of sodium chloride, 3 g of sodium sulfite, 150 g of sodium polyphosphate, 50 g of sodium L-glutamate, 120 g of sugar, 300 g of the powdered white and 30 g of a spice (the control section) or 30 g of the above powder (the present invention section). 300 g each of the pickles were injected into 1 kg of hog hind leg meat, respectively, and after the tumbling for 18 hours, the hams were filled into air-permeable casings, dried at 60° C. for 30 minutes, smoked at 60° C. for 30 minutes and steam-boiled at 75° C. for 60 minutes to prepare roast hams.

These products were preserved at 5° C. overnight, sliced, left standing in a room under scattered light for 3 hours and inspected for the appearance, whereby the present invention section showed red appearance and lessened discoloration, thus being better, as compared with the control section.

EXAMPLE 8

In a mixer, 700 g of the compound of the formula [I] wherein $R_1 = -(CH_2)_{16}CH_3$ as obtained in Example 1 was mixed with 300 g of cottonseed salad oil to prepare an oil solution.

700 g of hog lean meat, 300 g of lard, 10 g of sodium chloride, 5 g of sodium L-glutamate and 3 g of spice were mixed, and the mixture was divided into 100 g portions and formed to prepare meat pies. On the other hand, the above mixture was admixed with 0.8 g of the above oil solution, and meat pies were prepared in the same way. After the freeze-preservation at $-20°$ C. for 3 months, the oil-solution added section was less rancid flavored in flavour, as compared with the control.

What we claim is:

1. An ascorbic acid derivative of the formula:

wherein $R_1$ is a $C_{5-22}$ straight-chain or branched alkyl group, a $C_{1-10}$ straight-chain or branched alkyl group which has one to three substituent(s), the substituent being the class consisting of (1) $C_{1-6}$ alkoxycarbonyl, (2) phenyl which may have one to three substituent(s) of the class consisting of $C_{1-5}$ alkyl, $C_{1-3}$ alkoxy, halogen, nitro, amino, oxo, hydroxyl and benzyloxy, (3) aralkyl which may have one to three substituent(s) of the class consisting of $C_{1-5}$ alkyl, $C_{1-3}$ alkoxy, halogen, nitro, amino, oxo, hydroxyl and benzyloxy, (4) phenylcarbonyloxy which may have one to three substituent(s) of the class consisting of $C_{1-5}$ alkyl, $C_{1-3}$ alkoxy, halogen, nitro, amino, oxo, hydroxyl and benzyloxy, (5) aralkylcarbonyloxy which may have one to three substituent(s) of the class consisting of $C_{1-5}$ alkyl, $C_{1-3}$ alkoxy, halogen, nitro, amino, oxo, hydroxyl and benzyloxy, (6) 2,3,5-trimethyl-1,4-benzoquinoyl, (7) 2,3-dimethoxy-5-methyl-1,4-benzoquinoyl and (8) 2-methyl-1,4-naphthoquinoyl, a $C_{2-20}$ alkenyl group which may have one to three substituent(s), the substituent being the class consisting of phenyl, naphthyl, aralkyl, 3-pyridyl, thienyl and furyl, a phenyl, naphthyl or aralkyl group which may have one to three substituent(s), the substituent being the class consisting of $C_{1-5}$ alkyl, methoxy, methylenedioxy and hydroxyl, a $C_{1-9}$ acyl group of the class consisting of formyl, acetyl, propionyl, n-butyryl, isobutyryl, benzoyl, morpholinocarbonyl, $C_{1-3}$alkoxy-carbonyl-pyrrolidinocarbonyl, $C_{1-3}$alkoxy-carbonyl, phenylcarbonyl, phenylcarbonyl which have one to three substituent(s) of the class consisting of hydroxyl $C_{1-5}$alkyl and $C_{1-5}$alkyl and $C_{1-3}$alkoxy, arakylcarbonyl and aralkylcarbonyl which have one to three substituent(s) of the class consisting of hydroxyl $C_{1-5}$alkyl and $C_{1-3}$alkoxy, or a phenyloxy or aralkyloxy group which may have one to three substituent(s), the substituent being the class consisting of hydroxyl, $C_{1-5}$alkyl group and $C_{1-3}$ alkoxy group.

2. A compound as claimed in claim 1, wherein $R_1$ is $-(CH_2)_{13}CH_3$.

3. A compound as claimed in claim 1, wherein $R_1$ is $-(CH_2)_{16}CH_3$.

4. A compound as claimed in claim 1, wherein $R_1$ is $-(CH_2)_{18}CH_3$.

5. A compound as claimed in claim 1, wherein $R_1$ is —$(CH_2)_9COOCH_3$.

6. A compound as claimed in claim 1, wherein $R_1$ is

7. A method for producing an ascorbic acid derivative according to claim 1, which comprises subjecting a 5,6-acetal or ketal derivative of a compound of the formula:

wherein $R_1$ is as defined above and $R_2$ is a group removable by hydrolysis and/or reduction, to hydrolysis and/or reduction.

8. An antioxidant preparation for food which contains effective amount of an ascorbic acid derivative according to claim 1 and a diluent or carrier therefor.

9. An ascorbic acid derivative of the formula:

wherein $R_1$ is
a $C_{5-22}$ straight-chain or branched alkyl group,
a $C_{1-10}$ straight-chain or branched alkyl group which is substituted with either a $C_{1-6}$ alkoxycarbonyl or a $C_{2-20}$ alkenyl group.

* * * * *